US009770184B2

(12) United States Patent
Lappalainen et al.

(10) Patent No.: US 9,770,184 B2
(45) Date of Patent: Sep. 26, 2017

(54) ARRANGEMENT AND METHOD FOR CARRYING OUT ELECTRODE MEASUREMENTS

(71) Applicant: Bittium Biosignals Oy, Kuopio (FI)

(72) Inventors: Reijo Lappalainen, Hiltulanlahti (FI); Esa Mervaala, Kuopio (FI); Katja Myllymaa, Kuopio (FI); Sami Myllymaa, Kuopio (FI); Juha Toyras, Kuopio (FI)

(73) Assignee: BITTIUM BIOSIGNALS OY, Kuopio (FI)

( * ) Notice: Subject to any disclaimer, the term of this patent is extended or adjusted under 35 U.S.C. 154(b) by 69 days.

(21) Appl. No.: 14/710,290

(22) Filed: May 12, 2015

(65) Prior Publication Data

US 2015/0238106 A1     Aug. 27, 2015

Related U.S. Application Data

(63) Continuation of application No. PCT/FI2013/051054, filed on Nov. 7, 2013.

(30) Foreign Application Priority Data

Nov. 12, 2012   (FI) .................................... 20126186

(51) Int. Cl.
*A61B 5/0478*   (2006.01)
*A61B 5/00*     (2006.01)
(Continued)

(52) U.S. Cl.
CPC .......... *A61B 5/0478* (2013.01); *A61B 5/0408* (2013.01); *A61B 5/0496* (2013.01);
(Continued)

(58) Field of Classification Search
CPC ......................... A61B 5/0478; A61B 5/04085
See application file for complete search history.

(56) References Cited

U.S. PATENT DOCUMENTS 4,595,013 A  *  6/1986  Jones ................. A61B 5/04085
                                              600/383
6,032,065 A      2/2000  Brown
(Continued)

FOREIGN PATENT DOCUMENTS

EP      1 493 383 A2     1/2005
EP      0 951 233 B1     3/2005
(Continued)

OTHER PUBLICATIONS

International Search Report (PCT/ISA/210) mailed on Feb. 19, 2014, by the European Patent Office as the International Searching Authority for International Application No. PCT/FI2013/051054.
(Continued)

*Primary Examiner* — Lee S Cohen
(74) *Attorney, Agent, or Firm* — Buchanan Ingersoll & Rooney PC

(57) ABSTRACT

An arrangement is disclosed for carrying out electrode measurements on the surface of the skin of a patient's head for recording the electrical activity of the brain, the arrangement including a matrix electrode configuration, which includes a body part of non-conductive material conforming to the contours of the surface of the skin. The arrangement includes electrodes for producing the measurement data connected to the body part, means for transmitting the measurement data connected to the body part, and a measurement data unit for receiving the measurement data transmitted by the means for further processing of the measurement data. The body part can include an electrode placement configuration for maintaining the mutual placements of the electrodes with respect to one another and an
(Continued)

active attachment surface located between the electrodes and the surface of the skin to produce measurement data.

16 Claims, 3 Drawing Sheets

(51) Int. Cl.
   *A61B 5/0496* (2006.01)
   *A61B 5/0408* (2006.01)
(52) U.S. Cl.
   CPC ............ *A61B 5/684* (2013.01); *A61B 5/6814* (2013.01); *A61B 5/6823* (2013.01); *A61B 5/6832* (2013.01); *A61B 5/04087* (2013.01); *A61B 2562/046* (2013.01); *A61B 2562/14* (2013.01); *A61B 2562/164* (2013.01); *A61B 2562/182* (2013.01)

(56) References Cited

U.S. PATENT DOCUMENTS

| | | | |
|---|---|---|---|
| 6,066,093 A | 5/2000 | Kelly et al. | |
| 6,512,940 B1* | 1/2003 | Brabec | A61B 5/0031 600/374 |
| 7,515,950 B2* | 4/2009 | Healy | A61B 5/04087 600/391 |
| 8,473,024 B2* | 6/2013 | Causevic | A61B 5/0006 600/383 |
| 8,818,482 B2* | 8/2014 | Phillips | A61B 5/04085 29/825 |
| 8,821,397 B2* | 9/2014 | Al-Ali | A61B 5/0478 600/301 |
| 9,095,268 B2* | 8/2015 | Kurtz | A61B 5/0478 |
| 9,220,436 B2* | 12/2015 | Sandmore | A61B 5/0478 |
| 2002/0161309 A1 | 10/2002 | Marro | |
| 2003/0225323 A1 | 12/2003 | Kiani et al. | |
| 2005/0004489 A1 | 1/2005 | Sarkela et al. | |
| 2005/0277819 A1 | 12/2005 | Kiani et al. | |
| 2008/0146958 A1 | 6/2008 | Guillory et al. | |
| 2009/0018427 A1 | 1/2009 | Causevic et al. | |
| 2009/0105577 A1 | 4/2009 | Wu et al. | |
| 2009/0247894 A1 | 10/2009 | Causevic | |
| 2010/0036275 A1 | 2/2010 | Alkire | |
| 2010/0041962 A1 | 2/2010 | Causevic et al. | |
| 2012/0083673 A1 | 4/2012 | Al-Ali et al. | |
| 2015/0011857 A1* | 1/2015 | Henson | A61B 5/00 600/383 |

FOREIGN PATENT DOCUMENTS

| | | |
|---|---|---|
| WO | WO 01/30232 A2 | 5/2001 |
| WO | WO 03/057030 A1 | 7/2003 |
| WO | WO 2007/038305 A2 | 4/2007 |
| WO | WO 2009/061920 | 5/2009 |

OTHER PUBLICATIONS

Finnish Search Report for FI 20126186 dated May 24, 2013.

* cited by examiner

ARRANGEMENT AND METHOD FOR CARRYING OUT ELECTRODE MEASUREMENTS

RELATED APPLICATION(S)

This application is a continuation of International Application No. PCT/FI2013/051054 filed on Nov. 7, 2013, and claims priority to Finnish Application No. 20126186 filed on Nov. 12, 2012, the entire content of both of which is incorporated herein by reference.

FIELD

The disclosure generally relates to the field of medical technology, for example, to electroencephalogram (EEG) measurement.

BACKGROUND INFORMATION

The electrical activity of the brain can be examined by means of electroencephalography (EEG). Changes in the membrane stresses of neurons of the brain can be recorded by electrodes attached to the patient's scalp. When changes take place simultaneously in several neurons, the voltage fluctuations in single neurons can be summed and a measurable EEG signal can be produced. In practice, a signal recorded from the scalp originates from simultaneous changes in the post-synaptic potentials of the pyramidal neurons of the cortex. The voltage fluctuation in an EEG can be typically 5-250 µV and the frequency range can be 1-70 Hz.

EEG examinations can be used, for example, in specialised neurophysiological units in diagnosing epilepsy. There, the EEG recording can be carried out by specialist staff with high-level training and experience in using measuring devices and in the correct placement of the electrodes. However, EEG recordings could also be useful outside units specializing in EEG, for example, in an intensive care, paramedic care, and health centers, where by means of recordings could detect various disorders in the electrical activity of the brain relating to, for example, severe brain damage, cerebral infarction, cerebral haemorrhage, subarachnoid haemorrhage, intoxication and unclear consciousness disorders. For example, in paramedic care, the electrical activity of the heart (ECG) is recorded routinely, but the electrical activity of the brain, the EEG, is rarely recorded. The reason for this could be presumably the clumsy EEG sensor applications on the market, which can be slow and difficult to correctly place on the patient without specialised training and extensive experience. The lack of EEG monitoring currently presents a central diagnostic challenge, for example, in emergencies and in paramedic care, often hardly anything is known about the patient's brain activity or possible damage to the brain until the patient may have been moved to a hospital and to EEG monitoring. It would be desirable to be able to diagnose a dysfunction in the electrical activity of the brain as soon as possible and quickly start the appropriate treatment.

Currently, the EEG is most commonly measured by using an internationally standardised, so-called 10-20 system. As electrodes can be most often used cup electrodes made of, for example, silver-silver chloride (Ag—AgCl), silver, tin, gold or platinum. The 10-20 system can have several disadvantages, for example, the system uses 21 different electrodes, the positions of which in relation to the skull should be determined accurately, in order to be able to make a reliable diagnosis. A measuring wire connected to each electrode makes the measuring connection rigid and uncomfortable, hindering the patient's normal movements, and can cause interferences (movement artifacts) in the measuring signal and thus complicate the interpretation of the EEGs. Placing cup-like electrodes on the scalp can require preparation of the skin, that is, mechanical scraping of the skin to remove the dead surface layer (epidermis), and dosing of a conductive medium (electrode gel). Finally, the adhesion of the electrodes can be ensured by different attachment systems, such as tapes, bands, nets, caps or adhesive fixing paste. Thus, experience and special knowledge can be needed for measurement preparation. In addition, known equipment uses a considerable amount of time (for example, 30-50 minutes), thus delaying the initiation of the patient's proper treatment and considerably increasing the treatment costs.

Many of the current clinically used electrodes may not be compatible with magnetic imaging (MRI) and computed tomography (CT) equipment, and thus the electrodes have to be removed from the patient to help ensure safety and imaging quality. Removing and reattaching the electrodes can cause a long time-wise interruption in the EEG recording, in which case a clinically significant abnormality in the EEG can be undetected, leading in the worst case to an incorrect diagnosis. The removal and reattachment of the electrodes also can cause the patient to experience skin irritation, pain and a potential risk of skin infections.

Commercially (for example, in patent publication EP0951233 B1) available disposable electrodes, which can be adhered to the forehead, which can have only a few, for example, one to four (1-4), measuring channels and are mainly used for determining the depth of anaesthesia during operations. Due to the small number of electrodes, such solutions can be, however, unsuitable for diagnosing disorders in brain activity, for example, epilepsy, coma, cerebral hemorrhages.

One known solution is a quick-to-use matrix electrode (StatNet™, HydroDot Inc., WO2009/061920 A1), which consists of two strips placed crosswise over the head. The strips have a sandwich structure with silver-silver chloride electrodes and silver signal transmission lines integrated in flexible plastic film. In each strip, the transmission lines end on the edge of the strip, from where the signals measured can be led by means of a quick coupling to an amplifier. The strips can be coated with an adhesive by means of which the sensor remains adhered to the skin by itself. On top of the electrodes can be a porous pre-moistened pad construction. No preparation of the skin or other pre-treatment can be thus needed. The set-up time of the sensor can be, for example, 5 minutes, and the operating time of the electrodes can be, for example, 4 hours. StatNet's sensor, for example, is placed over the hair and is structurally relatively rigid (bends only in the direction of the strip), conforms poorly to surfaces curving in several directions, moves easily with the hair, and uses monitoring to ensure that it has remained in place. This sensor application is also unsuitable for patients whose head or neck should not be moved or who have injuries or measuring instruments in the cranial area. The known implementation may be suitable for paramedic and intensive care unit use, but not for several other EEG examinations, such as long-term epilepsy studies or sleep studies.

U.S. Pat. No. 6,032,065 A discloses a disposable EEG matrix electrode for use in the hairless areas of the face. The substrate can be made of a non-conductive polymer, such as Mylar. In the publication, the ground electrode is located centrally, the reference electrode on the neck, and the movement of the eyes and the EMG signal from the chin can be monitored by means of the electrodes. There are only two EEG electrodes on the temples. In this known implementation, a separate medium (electro-gel) can be used to affix the electrodes on the surface of the skin and to form a proper electrode contact.

U.S. Patent publication No. 2010/0041962 A1 discloses a matrix electrode intended for EEG monitoring, which includes electrode contacts placed on the hairless areas of the face. The publication shows a sensor construction, which makes possible lateral extension of the sensor in order for the sensor construction to fit the different face sizes of patients. The mutual placement of the electrodes with respect to one another changes when attached to faces of different size. In addition, stable attachment of the sensor construction can be ensured with a separate adhesive layer. The attachment of the sensor construction can be ensured with a structure extending behind the ear.

SUMMARY

An arrangement is disclosed for carrying out electrode measurements on a surface of a skin of a patient's head for recording electrical activity of the brain, the arrangement, comprising: a matrix electrode configuration, which includes a body part of non-conductive material conforming to contours of the surface of the skin, and which arrangement includes electrodes for producing measurement data connected to the body part; means for transmitting the measurement data connected to the body part; a measurement data unit for receiving the measurement data transmitted by the means for further processing of the measurement data, and which body part includes an electrode placement configuration for maintaining mutual placements of the electrodes with respect to one another, and an electroconductive active attachment surface located between the electrodes and the surface of the skin for forming an electroconductive attachment contact between the electrodes and the surface of the skin for transmitting measurable signals from the patient's head to the electrodes through the electroconductive active attachment surface to produce measurement data, the electroconductive active attachment surface including hydrogel or other electroconductive adhesive material which adheres to the skin in order to form a stable and essentially interference-free attachment contact between the electrodes and the surface of the skin; an electrode configuration of spiral structure being in contact with hairless skin areas through the electroconductive active attachment layer; and a grounding layer formed completely or partly over the body part to prevent external electrical interferences by isolating the grounding layer with an isolation layer from the electroconductive active attachment surface and the means for transmitting the measurement data.

A method is disclosed for carrying out electrode measurements on a surface of a skin of a patient's head for recording electrical activity of the brain, the method, comprising: placing a matrix electrode configuration on the surface of the skin of the patient head, wherein the matrix electrode configuration comprising: a body part of non-conductive material conforming to contours of the surface of the skin, and which includes electrodes for producing measurement data connected to the body part, an electrode placement configuration for maintaining mutual placements of the electrodes with respect to one another, an electroconductive active attachment surface located between the electrodes and the surface of the skin for forming an electroconductive attachment contact between the electrodes and the surface of the skin for transmitting measurable signals from the patient's head to the electrodes through the electroconductive active attachment surface to produce measurement data, the electroconductive active attachment surface including hydrogel or other electroconductive adhesive material which adheres to the skin in order to form a stable and essentially interference-free attachment contact between the electrodes and the surface of the skin, an electrode configuration of spiral structure being in contact with hairless skin areas through the electroconductive active attachment layer, and a grounding layer formed completely or partly over the body part to prevent external electrical interference by isolating the grounding layer with an isolation layer from the electroconductive active attachment surface and a means for transmitting the measurement data; transmitting the measurement data connected to the body part to a measurement data unit; receiving the measurement data on the measurement data unit and processing the measurement data.

DETAILED DESCRIPTION

Figure 1:
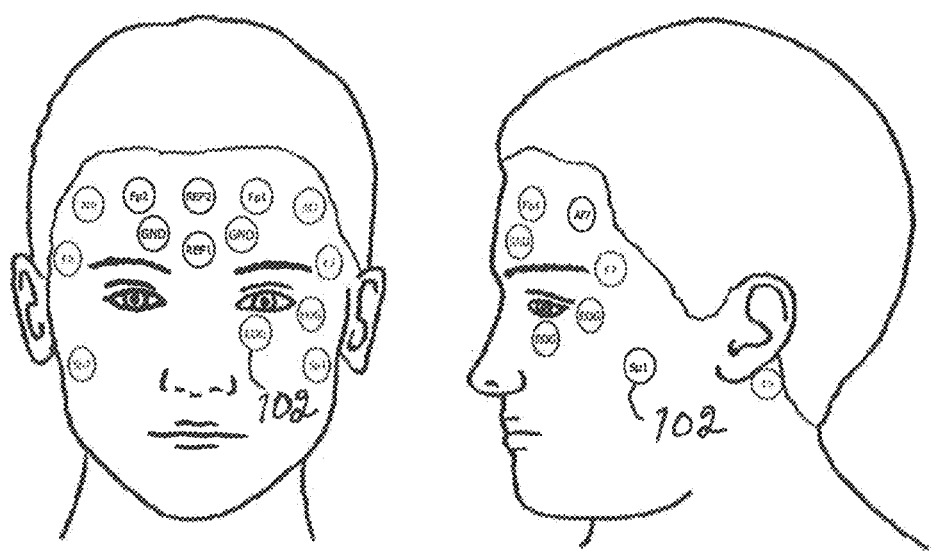
FIG. 1 shows an exemplary placement of the electrodes of the matrix electrode configuration in the hairless areas of the patient's head.

In accordance with an exemplary embodiment, the present disclosure can help eliminate and reduce the problems relating to the known EEG electrode solutions disclosed, which can include the difficult and slow placement of the electrodes, to instable skin contact, to the drying of the electrodes (for example, increase in measuring resistance, for example, impedance), to noise and interference levels, and to incompatibility with magnetic imaging (MRI) and computed tomography (CT) equipment.

In accordance with an exemplary embodiment, the present disclosure relates to an electrode measurement implementation for recording the electrical activity of the brain on the surface of the skin of the patient's head, by means of which implementation electrode measurements can be substantially facilitated and speeded up to produce high-quality measurement data for examination or monitoring, which can be achieved by means of an arrangement for carrying out electrode measurements on the surface of the skin of a patient's head for recording the electrical activity of the brain, the arrangement including a matrix electrode configuration, which includes a body part of non-conductive material conforming to the contours of the surface of the skin, and which arrangement includes electrodes for producing the measurement data connected to the body part, means for transmitting the measurement data connected to the body part, and a measurement data unit for receiving the measurement data transmitted by the means for further processing of the measurement data. The body part can include an electrode placement configuration for maintaining the mutual placements of the electrodes essentially the same with respect to one another, and the arrangement can include an active attachment surface located between the electrodes and the surface of the skin for forming a firm and electroconductive attachment contact between the electrodes and the surface of the skin for transmitting measurable signals from the patient's head to the electrodes through the electroconductive active attachment surface to produce measurement data.

In accordance with an exemplary embodiment, a method is disclosed for making electrode measurements for carrying out recording of the electrical activity of the brain from the surface of the skin of the patient's head, in which method can use a body part of an electrode configuration which is of non-conductive material conforming to the contours of the surface of the skin, the measurement data is produced by measuring with electrodes, the measurement data is transmitted from the electrodes to the measurement data unit for further processing of the measurement data. In accordance with an exemplary embodiment, electrodes can be placed, using the electrode placement configuration, on the surface of the skin of the patient's head by maintaining the mutual placements of the electrodes essentially the same with respect to one another, and a firm and electroconductive attachment contact is formed by means of an active attachment surface between the electrodes and the surface of the skin for transmitting the measurable signals from the patient's head to the electrodes through the electroconductive attachment contact for producing measurement data.

In accordance with an exemplary embodiment, the disclosure is based on the utilisation of the type of matrix electrode configuration in which can be implemented an electrode placement configuration for maintaining the mutual placement of the electrodes with respect to one another essentially the same. The actual attachment of the electrodes to the mutual placements of the electrodes in the object of measurement can be carried out by means of an active attachment surface located between the electrodes and the surface of the skin to form a firm and electroconductive attachment contact between the electrodes and the surface of the skin. The active attachment surface can include an electroconductive surface and a non-conductive surface separately. Through the attachment contact can be transmitted measurable signals from the patient's head to the electrodes for producing measurement data.

In accordance with an exemplary embodiment, rapid and reliable attachment of the matrix electrode configuration can be provided in the hairless areas of the patient's head in such a way that the real mutual placement of the electrodes is known. Both the successful electroconductive attachment of the electrodes and the correct and desired placement of the electrodes can produce high-quality measuring information.

In this context, the word "hair" is supposed to mean only the hair growing from persons head, which can grow into length of dozens of centimeters if not specifically cut. This term should not be understood to mean the fluffy skin hair around the human body, neither is it supposed to mean any facial hair or other male or female typical hair growth on the skin. It is to be understood, that the hairless areas of the skin can include skin hair or facial hair.

Figure 2:
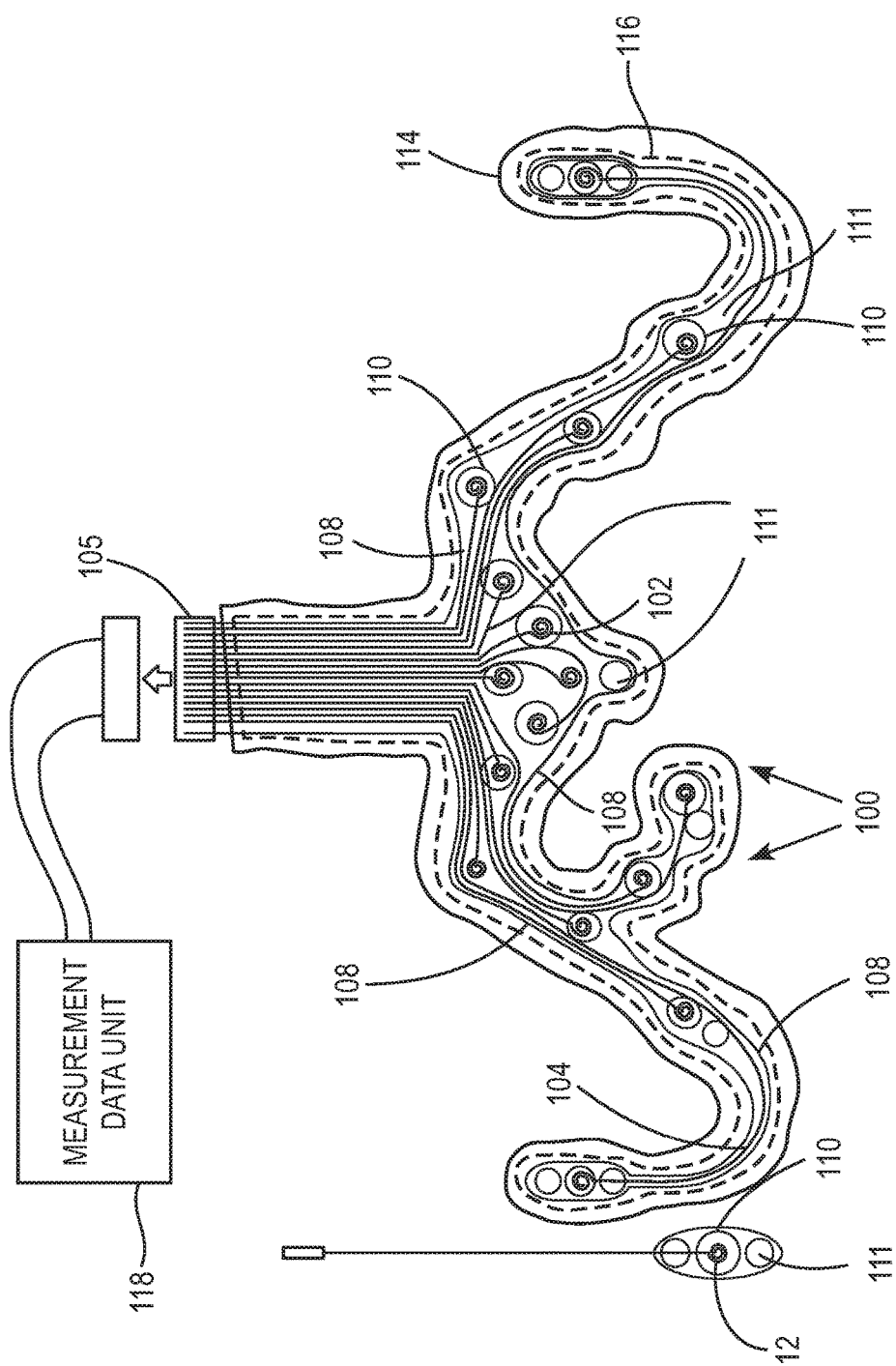
FIG. 2 shows an exemplary embodiment of the disclosure of an arrangement for carrying out electrode measurements.

In accordance with an exemplary embodiment, the arrangement according to the present disclosure for carrying out electrode measurements, electrical activity of the brain is measured on the surface of the skin of the patient's head to produce measurement data. The measurement data can be stored for assessment of the electrical activity of the brain. FIG. 2 shows an exemplary embodiment according to the disclosure of an arrangement for carrying out electrode measurements. The arrangement can include a matrix electrode configuration, which can include a body part 100 of non-conductive material conforming to the contours of the surface of the skin. The body part 100 can be connected electrodes 102 for producing the measuring data. The means 104 for transmitting the measurement data can be connected to the body part 100. The means 104 can be, for example, conductor lines, for example, to a ZIF-type quick coupling 105 through which the measurement data is transmitted further through a wire or wirelessly to a measurement data unit for further processing of the measurement data. The measurement data unit can be, for example, a computer unit for diagnostic examinations.

FIG. 1 shows an exemplary placement of the electrodes of the matrix electrode configuration in the hairless areas of the patient's head. The body part 100 (FIG. 2) according to the disclosure can include an electrode placement configuration 108, by means of which the mutual placements of the electrodes 102 can be maintained essentially the same with respect to one another. The arrangement according to the disclosure can also include an active attachment surface 110 located between the electrodes 102 and the surface of the skin for forming a firm and electroconductive attachment between the electrodes and the surface of the skin, by means of which attachment contact can be transmitted measurable signals from the patient's head to the electrodes through the electroconductive active attachment surface 110 for producing measurement data. In accordance with an exemplary embodiment, the active attachment surface can also include an area or areas 111, which can be of non-conductive material, which adheres to the skin, which can include hydrogel or other substance or component with similar properties.

In an exemplary embodiment of the disclosure, the body part 100 can include the electrode placement configuration 108 for relatively easy attachment of the matrix sensor construction in the hairless skin areas of the patient's head by means of the active attachment surface 110. In this case, each electrode can attach to its intended measuring point in the hairless skin areas of the head. The electroconductive active attachment surface 110, for example, can include hydrogel in order to form a stable and essentially interference-free attachment contact between the electrodes 102 and the skin surface. Completely or partly over the body part 100 can be formed a grounding layer 114 to prevent the effect of external electrical interferences. The grounding layer 114 can be isolated by an isolation layer and/or the body part from the active attachment surface 110 and the wires. If there are no holes in the body part, it can act as isolation. If there are holes in the body part, isolation can be provided by a separate layer 116. In accordance with an exemplary embodiment, the grounding layer 114 functions can prevent the induction of electrical interferences to the wires and thus to the measured EEG signal, for example, the measurement data that is transmitted to the measurement data unit for further processing of the measurement data.

The matrix electrode configuration can, for example, include at least two reference electrodes 102 and, for example, at least two ground electrodes 102, between which can, when measuring, be selected which electrode combination is used to produce the measurement data. If the electrode contact is good, the matrix electrode configuration can also include only one reference electrode and only one ground electrode. The grounding layer can be connected to the ground electrode or ground electrodes. In accordance with an exemplary embodiment, matrix electrode configurations can be scaled to fit optimally different sizes of heads without the scaling affecting the number of electrodes used.

Figure 4:
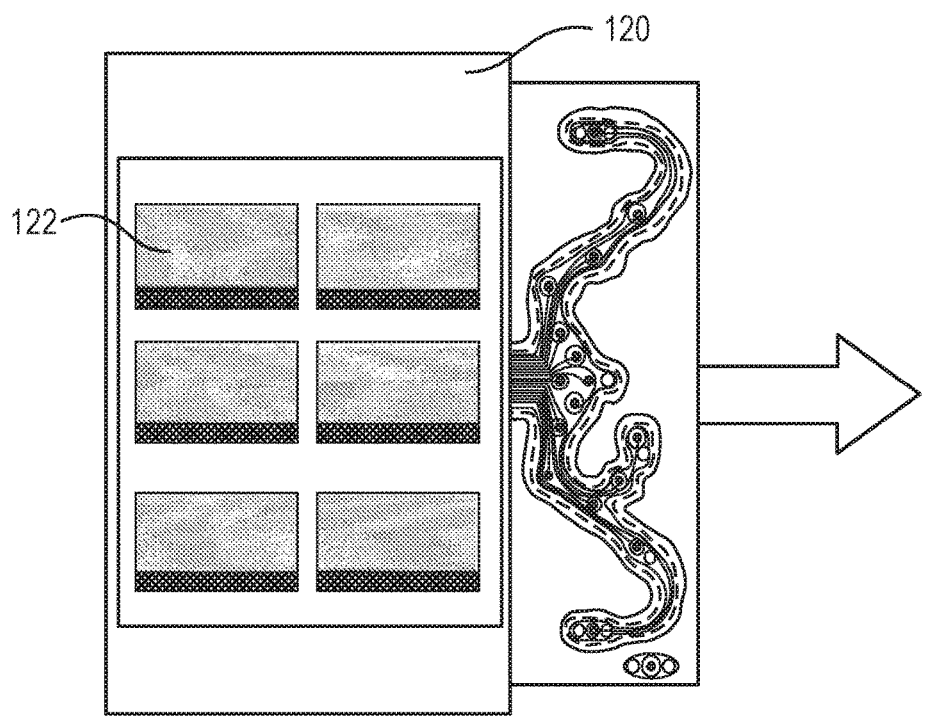
FIG. 4 shows an example of a package in accordance with an exemplary embodiment.

As shown in FIG. 4, the arrangement according to the disclosure can include at least the matrix electrode configuration packed into a package 120, on the outside of which can be seen dimensioning indicators 122 for ensuring the correct matrix electrode configuration size to fit the patient's head without opening the package.

Figure 3:
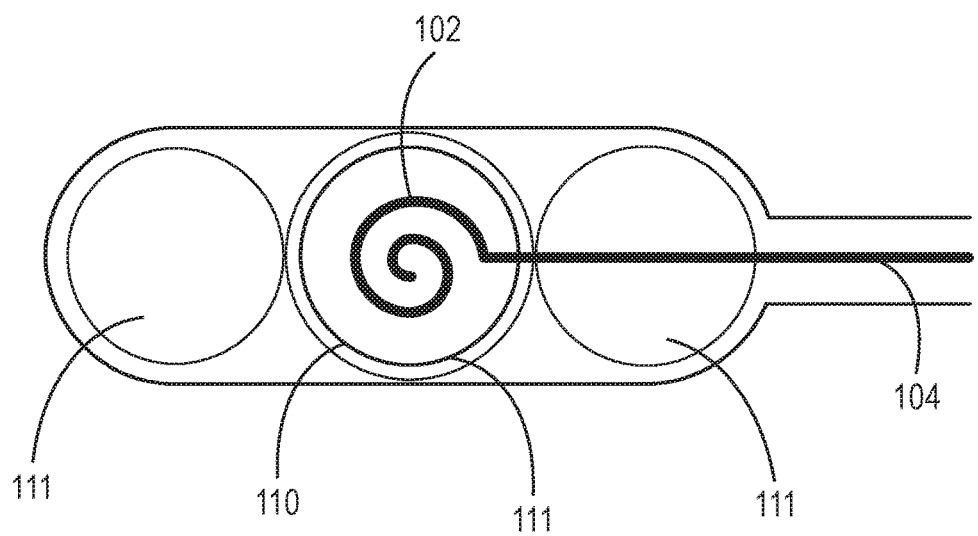
FIG. 3 shows an example of a spiral electrode configuration made with printing technique in accordance with an exemplary embodiment.

In accordance with an exemplary embodiment, the signal-to-noise ratio (S/N) can be improved by forming and using an optimized electrode configuration to provide an essentially good signal-to-noise ratio (S/N), as well as MRI and CT imaging compatibility. In accordance with an exemplary embodiment, the optimized electrode configuration can be, for example, a spiral matrix electrode configuration. FIG. 3 shows an example of a spiral electrode configuration 102 produced by printing technique. The area 111 surrounding the electrode 102, and the separate circular areas 111 in the examples according to FIGS. 2 and 3, represent areas 111 of the active attachment surface with non-conductive material attaching to the skin surface, the material including hydrogel or other substance or composition with the corresponding properties.

In addition, the arrangement for carrying out electrode measurements can include at least one electrode 112 attached in the patient's chest area for carrying out cardiac measurements (ECG).

In the following can be described, with reference to FIGS. 1-3 or at least some of them, different possible uses and embodiments of the disclosure. From here onwards, the matters disclosed in this detailed description can be, thus examples of the various possible implementations and properties of the different parts 100, 102, 104, 105, 106, 108, 110, 112 of the disclosure. According to the present disclosure is thus realised a matrix electrode configuration including a body part 100 conforming to the contours of the face, which body part can be made of non-conductive material, for example, polyester film, and to which the electrodes 102 and the measurement data transmission wires 104 can be integrated. Thanks to the body part, the positions of the electrodes with respect to one another remain essentially unchanged and positioning the electrodes in the correct places on the patient's face and elsewhere is easier. The electrodes fixed to the body part can be placed in the hairless areas on the patient's forehead, temples, cheeks and bridge of the nose, as well as behind the ears. In addition, one electrode can be placed on the chest for ECG monitoring.

The matrix electrode can be designed to be attached directly onto cleansed skin and to cover all essential EEG measurements normally made in hairless head areas. Separate gels or electrode pastes are not needed and may not be used for attachment. In accordance with an exemplary embodiment, the active attachment surface based on hydrogel immediately can provide a stable contact with the skin, which can last for days. From the point of view of manufacturing technique and structure, the matrix electrode can be relatively simple and economical and thus suitable to be disposable. The matrix electrode can be delivered sterilised in a disposable package.

In an exemplary matrix electrode configuration, the wires 104 can be silver-plated Aracon fibre. The electrodes 102 can be spiral (diameter 7 mm) structures made of silver wire, which can be coated with an electroconductive hydrogel film. The matrix electrode can include, for example, a total of 16 electrodes, of which, for example, ten (10) can be EEG measuring electrodes (in the Figure Fp1, Fp2, Af7, Af8, F7, F8, Sp1, Sp2, T9 and T10), two (2) can be EOG electrodes (identification of eye movements, in the Figure "EOG" and "EOG"), two (2) can be reference electrodes (REF), and two (2) can be ground electrodes (GND). The electrodes 102 can be spiral structures (102, FIG. 3) at the end of a conductive metal wire or fibre (for example, silver-plated isolated Aracon). In accordance with an exemplary embodiment, for example, the wire material can be highly electroconductive material, for example, silver, silver silver-chloride, gold or various alloys. A good contact of the electrodes with the skin can be relatively ensured with an electroconductive, for example hydrogel film, developed for medical use (for example AG602, Amgel Technologies). Skin attachment, if necessary, can be secured at desired points with skin tape. As support for the electrodes, a thin film conforming to the contours of the face can be used, which film can be, for example, polyamide, polyimide (Kapton), polyester (Mylar), or other elastic material.

The electrodes according to the disclosure can be designed to be attached directly onto cleansed skin and to cover all essential EEG measurements normally made in hairless head areas. Separate gels or electrode pastes are not needed and may not be used for attachment. The active attachment surface based on hydrogel immediately provides a stable contact with the skin, which can last for days.

The matrix electrode configuration according to the disclosure can be formed, for example, by a method of implementation based on lamination technique. The sensor implementation can have a sandwich structure, including, for example, the following layers when viewed from the outside towards the patient's skin: stiffener layer (1), grounding layer (2), base layer (3), conducting layer (4), insulant layer (5), hydrogel layer (6), and release liner layer (7). As the body part (base layer) of the matrix electrode is used, a thin polymer film, such as Mylar, which conforms to the contours of the face. The electrodes 102 and their transmission lines 104 (conducting layer) can be thick-film structures made of conductive ink (for example Ag/AgCl ink) on the surface of the Mylar. The body part of the matrix electrode can be coated with an insulating material (insulant layer) to avoid short-circuiting of the wires. In the insulating material can be openings at the electrodes, through which the electrode spirals can be in contact with the hydrogel (for example, AG602, Amgel Technologies, Fallbrock, Calif., USA). The release liner layer can be a protective film layer, which protects the electrodes from drying. In accordance with an exemplary embodiment, the protective film can be, for example, a thin plastic film, which is torn off at the stage when the attachment of the electrode is begun.

In accordance with an exemplary embodiment, each of the transmission lines ends in the sensor's projecting part, from which the measured signals can be guided by means of a quick coupling to an amplifier. A coupling can be used, which can be either an MRI-compatible coupling or an easily disconnected/reconnected coupling, for example so-called ZIF-type connector. The conductor layer can be covered by an insulating layer (insulant layer) with oval openings at the spiral electrodes. A good contact of the electrodes with the skin can be ensured by areas of hydrogel film attached at the electrodes. In accordance with an exemplary embodiment, a booster is in addition used non-conductive hydrogel around each electrode (hydrogel layer or other adhesive material) to facilitate the placing of the extremely flexible sensor on the patient's skin and to ensure good attachment. The hydrogel layer can be covered with a protective layer (release liner layer) which gives support during the mounting of the electrode. The matrix electrode can include a total of 17 electrodes, ten (10) of which can be EEG measuring electrodes, two (2) can be EOG electrodes (identification of eye movements), two (2) can be ground electrodes (GND), two (2) can be reference electrodes (REF) and one (1) is an ECG electrode (measurement of the electrical activity of the heart) placed on the chest.

In view of the exemplary implementations 1 and 2, it may be obvious to a person skilled in the art that the matrix electrode described in the disclosure can be implemented with very different techniques, for example, with thin film and lithographic methods, silk-screen printing technique, printing techniques, various lamination techniques, etc.

The arrangement according to the disclosure for carrying out electrode measurements can be utilised and used, for example, in the following applications and with them can be achieved, for example, the functional improvements disclosed in the examples:

Example 1. Short-Term Monitoring, Advantage of Rapid Reliable Attachment of Headset, No Special Skills An unconscious patient is brought to an emergency department. A paramedic is able to attach the disclosure on the patient's forehead and face within a few minutes, without separate EEG nurse training. Thus, a general idea of the state of the patient's brain is obtained quickly. Changes in the EEG due to possible conditions requiring emergency care (for example, status epilepticus, subarachnoid haemorrhage, and infections in the central nervous system, as well as metabolic and toxicological disorders) can be detected immediately and the patient can be referred to the appropriate treatment as quickly as possible.

Example 2. Long-Term Monitoring

In accordance with an exemplary embodiment, the arrangement can be used in a hospital ward for long-term EEG monitoring to detect random abnormalities in a patient's EEG. In long-term monitoring, sudden deterioration of the patient's neurological status can be detected at the same time. The electrodes according to the disclosure can withstand long-term recording without drying, and without allergic reactions appearing on the skin. In accordance with an exemplary embodiment, the matrix electrode can be lightweight, flexible and breathable, and does not, therefore, cause the patient additional stress. For example, measurements can be carried out with a Telefactor electroencephalograph and the contact impedances of the electrodes and the measured signals can maintain a high quality throughout, for example, the measurements, for example, over a 48 hour period.

Example 3. Status Epilepticus

Status epilepticus (SE) is a life-threatening neurological state of emergency, which can require fast and efficient treatment. SE can be caused by excessive excretion of excitatory transmitters (glutamate) from their nerve endings. It is estimated that as many as 20% of the discharges can be non-convulsive, for example, do not cause observable convulsions. Therefore, without EEG measurement, a patient can be suffering from epileptic discharge activity without it being observed and treated. The disclosure provides a fast and easy way of verifying whether an unconscious patient is in a non-convulsive state. The matrix electrode can also be used during the loading of status epilepticus medication, in which case any cerebral or cardiac complications can be detected immediately. In addition, the matrix electrode can be used for monitoring the burst decay state used in the treatment of status epilepticus. The burst decay can be seen extremely well from the forehead electrodes.

Example 4. SAH Patient (Subarachnoid Haemorrhage)

An SAH patient is bleeding into the space between the arachnoid and the pia mater immediately surrounding the brain. A sudden severe headache can be one of the single most significant symptom of subarachnoid haemorrhage. Partly due to the lack of suitable, easy-to-use EEG electrodes, EEG monitors cannot be generally used in monitoring the status of SAH patients, although this has been reported as being of primary importance for successful treatment. The arrangement provides a fast and easy way of carrying out the monitoring of an SAH patient.

Example 5. Damage to Cranium or Cervical Spine, Normal EEG not Suitable; One Example of Intensive Care The patient was found unconscious in the street and can have, or is suspected to have, sustained an injury to the cranium or cervical spine. Normal EEG is not suitable because a conventional measuring connection cannot be attached on the injury. In addition, due to the injury, the patient's head cannot be moved and placing a conventional measuring connection could require movement of the head. The disclosure makes possible EEG measurement of this type of neck/head injury patient without having to move the patient's head or place the electrodes on the injury.

Example 6. Craniotomy

Craniotomy refers to a surgical procedure in which the skull is opened to gain access to the brain. Craniotomy can also be used for treating cerebral edema and increased intracranial pressure to reduce the pressure and give the brain room to swell. Different types of epileptic phenomena can be common in the EEG in this type of treatments. Using a normal EEG connection, however, can be impossible, because electrodes cannot be placed on the craniotomy. An easy-to-use matrix electrode fixed on the forehead and face can make EEG monitoring of this type of patient possible without endangering the patient's health.

Example 7. Isolation Patient (Disposability, Safety and Ease of Use)

A patient is suspected as having the Creutzfeldt-Jacob disease (CJD, commonly known as the "mad cow disease") and is in isolation. CJD can cause distinct changes in the EEG signal, and thus measurement can be extremely useful in identifying the disease. The disclosed arrangement can speed up and facilitate the measurement of such isolation patients. The disclosed arrangement can also reduce the risk of contamination because it is disposable, and quick and easy to attach. In accordance with an exemplary embodiment, the matrix electrode can be destroyed immediately after the recording.

Example 8. Patient can have Measuring Instruments Connected Through the Skull into the Brain, Normal EEG is Unsuitable In the intensive care unit, a patient can have various measuring devices (for example a microdialysis device or intracranial pressure meter) connected through the skull directly into the brain. In this case, however, it may be impossible to carry out normal EEG measurement. By means of the disclosed arrangement, measurement can be carried out, however, because the matrix electrodes can be placed on the patient's forehead and face instead of on the skull. Measurement carried out with the disclosed arrangement does not interfere with the other measuring devices and does not cause additional risks to the patient, because the measuring devices connected to the central nervous system do not have to be moved.

Example 9. Monitoring Following Resuscitation

When the heart stops or circulation to the brain is otherwise disrupted, there can be a risk of the patient sustaining temporary or permanent hypoxic ischemic encephalopathy due to lack of oxygen in the brain. Because the disclosure is easy and quick to attach, it provides a quick solution to EEG monitoring following resuscitation. By means of the disclosed arrangement, information on possible injuries can be obtained within a few minutes following the resuscitation. In accordance with an exemplary embodiment, the disclosed arrangement could be a standard accessory included in the resuscitation equipment so that the arrangement can be placed immediately after resuscitation.

Example 10. PLED (Periodic Lateralized Epileptiform Discharges)

In connection with severe brain damage, in the EEG signal can be observed PLED waves, which appear periodically. In some cases, a PLED wavelet can be confused with an ECG artifact and thus it is good to have also the ECG signal displayed next to the EEG. In contrast to other instant EEG solutions, in accordance with an exemplary embodiment, the disclosed arrangement can include a separate electrode for the ECG, which thus measures the electrical activity of the heart.

Example 11. Sensor for Depth of Anaesthesia

Because the use of the disclosed arrangement is easy and quick and in addition disposable, it can also be used for recording the EEG signal for the purposes of an anaesthesia monitor. The disclosed arrangement can be connected by means of a suitable adapter to an anaesthesia monitor and the depth of the anaesthesia can be read directly on the monitor's display using an electrode intended, for example, for said use. Because the disclosed arrangement is versatile, it is not necessary to buy several different sensors suitable for EEG measurement, for example, for intensive care units. In addition to the matrix headset according to the disclosure can be provided various adapter connectors, by means of which the headset can easily be connected to different types of EEG amplifiers and monitors.

Example 12. MRI Compatibility (Phantom Measurement)

In accordance with an exemplary embodiment, the arrangement according to the disclosure is not ferromagnetic. The MRI compatibility of the disclosure has been tested on an MRI phantom. The arrangement according to the disclosure does not warm up in an MRI imaging device or cause interference in MRI images. Therefore, the disclosed arrangement does not have to be removed for the duration of magnetic imaging, and EEG measurement can be continued immediately after the imaging. Normally, the EEG sensors have to be removed for the duration of the imaging, after which they have to be reattached if recording is to be continued, which can take extra time and can slow down the patient's referral to the appropriate care. In addition, the reattachment of the electrodes can involve a risk of abrading the skin, which can increase the risk of sustaining different allergic reactions or infections. The MRI compatibility of the disclosed arrangement can be relatively ensured with a disconnectable ZIF-type coupling, which can be easy to remove before imaging and the connection with the amplifier is reinstated by reattaching the ZIF coupling to the matrix electrode.

Example 13. CT Compatibility, Phantom

In accordance with an exemplary embodiment, the disclosed arrangement can be compatible with computed tomography imaging (CT). For example, the disclosed arrangement does not warm up in the CT device or cause significant interference in the images taken. Therefore, the disclosure does not necessarily have to be removed for the duration of CT imaging, and EEG measurement can be continued immediately after the imaging. Normally, the EEG sensors have to be removed for the duration of the imaging, after which they have to be reattached if recording is to be continued, which can takes time and can slow down the patient's referral to the appropriate care. In addition, the reattachment of the electrodes can involve a risk of abrading the skin, which can increase the risk of sustaining different allergic reactions or infections.

Example 14. Ambulance or Ambulance Helicopter Measurements

In accordance with an exemplary embodiment, because the disclosed arrangement is extremely easy to use, it can be used to carry out EEG recordings in field conditions, for example, in an ambulance or ambulance helicopter. For example, in practice, it can be appropriate to attach the matrix electrode to the patient in the ambulance, ambulance helicopter or in the army at a dressing station or in a field hospital. In this way, the state of the patient's brain and possible dysfunctions can be known before the patient arrives at the hospital. The EEG data can also be sent wirelessly to the hospital's data system, such that the patient can be referred to the appropriate care and started on the appropriate medication immediately on arrival at the hospital.

Example 15. Wireless Data Transfer Solutions

In accordance with an exemplary embodiment, the disclosed arrangement can be extremely light, easy to place and disposable. It is, therefore, highly usable as an EEG sensor for wireless EEG measuring solutions intended for various field solutions. Wireless solutions, for example, can be implemented by Bluetooth, wlan, GSM, 3G or infrcan bed techniques.

Example 16. EEG Use at Health Centre Level, Transmission of Results to Central Hospital In accordance with an exemplary embodiment, because the disclosed arrangement can be easy and quick to carry out EEG measurements, and no special skills are necessary to place the arrangement on the patient, the arrangement can be utilized by health centre nurses. In addition, the EEG can thus be measured immediately already at the health centre's on-call service without having to refer the patient to a central or university hospital for the recording. A neurophysiologist can read the EEG remotely through the Internet and the patient can be immediately referred to the appropriate care, which can be important in many cases where early treatment can improve the prognosis for recovery. With recordings at health centers can be potentially also saved considerable sums in transportation costs because the patients do not necessarily have to be transported from one hospital to another.

Example 17. Monitoring of Premature Infants

With very small premature infants, so-called amplitude-integrated EEG (aEEG) monitoring can be started immediately after birth in order to be able to detect possible epileptic activity. Electrodes currently used can include needle electrodes, which can be quick and easy to attach. However, when attaching them, the skin has to be pierced, which can increase the risk of sustaining different inflammations or infections. The disclosed arrangement, which is equally quick and easy to attach, can be used instead of needles, which can reduce the risk of inflammations and infections. In accordance with an exemplary embodiment, smaller versions of the disclosure can be made to fit premature infants.

Example 18. Paediatric Patients

Placing a conventional EEG connection on the head of an uncooperative child is a time-consuming, difficult and sometimes even an impossible task. In placing a conventional connection, the child's head usually also has to be scraped with a wooden applicator, which the child will find unpleasant. In addition, a child can have a fear of needles and will be afraid of being pricked when the nurse takes the scraping applicator out. Sometimes even sedatives have to be used to be able to attach the conventional connection, which can be undesirable because sedatives can affect the EEG signal to some extent. In accordance with an exemplary embodiment, placing the disclosed arrangement on the skin does not require scraping and thus cooperation with the child is much easier. Furthermore, placing the disclosed arrangement takes much less time and thus the child's patience lasts longer.

Example 19. Chronic Patients in Health Centers

In health centers, there can be many chronically ill elderly patients with considerable difficulties in communication, whose neurological status has not been assessed. The disclosure could provide a quick and easy way of measuring these patients by routine screening and to assess their status, for example, in a non-convulsive epileptic state.

Example 20. Alternative Ground and Reference Electrodes

Because one has to work in difficult conditions in paramedical situations, where a patient can be, for example, very dirty or restless, there can be two ground and reference electrodes in the disclosure. If one of the two is broken, it can be programmatically replaced by an unbroken one, and thus the functioning of the EEG recording can be ensured.

Example 21. Solutions Facilitating Use Contained in the Package

The headset package can be a part of the product facilitating its use, which can contain, for example, clear illustrated numbered instructions, a picture of the typical placement of the headset on the face, the means needed for cleansing the face (wet wipes, cleansing tape, . . . ), the means for tying up the hair (if the hair would otherwise be in the way, for example net, headset, fastening clips, . . . ), a coupling, etc. The outer surface of the package can be provided with, for example, a measuring scale, to function as a measuring indicator, which can be used (by trying the package on the patient's face), without opening the package, to estimate whether the model is suitable or whether a different modular size should be selected, and which can help one select the right size.

Example 22. Impedance Testing of Different Electrode Heads on the Skin

Preparation: in all cases cleansing with alcohol, light scraping with tape and moistening with 0.5% NaCl. As an example, a silver chloride cup electrode can be used, and the measurements of this exemplary implementation were carried out with a Telefactor EEG device. In this exemplary implementation, the spiral electrode gave the smallest contact impedance and the noise level of its signal was distinctly lower than with the other solutions.

The electrode implementation according to the disclosure, which attaches to the skin, can also be implemented by means of a suitable electroconductive adhesive. Such adhesives can be, for example, starch- and agar-based materials to which, for example, NaCl has been added to enhance electroconductivity.

Example 23. Comparison of Interference Levels

In accordance with an exemplary embodiment, the electrode used in the disclosure can provide a better signal-to-noise ratio than known electrodes, which can be due to the choice of materials used, for example, the active attachment surface 110 used including, for example, hydrogel and different shapes/patterns of the silver silver-chloride electrode (disc, elliptic disc, ring, loop, finger-like shape, snake-like shape, spiral shape, etc.). The electrode can also be extremely stable, and is not sensitive to interference caused by the patient's movements. These can be important properties in order to be able to detect the minute changes shown in the EEG.

In the following is described in detail an exemplary embodiment of the disclosure, that is, a new type of disposable matrix electrode for monitoring electrical activity of the brain (EEG), which can be utilised, for example, in paramedic care situations. In an acute situation, measuring an unconscious patient's EEG can be of importance in assessing the patient's status. In paramedic care, the electrical activity of the heart (ECG) is measured routinely, but the electrical activity of the brain rarely. The reason for this can be the clumsy sensor implementations on the market, which can be slow to place properly on the patient. With an EEG could, however, be detected various brain dysfunctions relating to, for example, severe brain damage, cerebral infarction, cerebral haemorrhage, subarachnoid haemorrhage, status epilepticus, intoxication and unclear consciousness disorders. Therefore, it can be essential to be able to diagnose brain-related disorders as early as possible and to initiate the relevant care quickly. The currently widely used EEG electrodes can be metal electrodes (SS, Ag—AgCl, Pt), which can be separate and adhered to the skin. The positions of the electrodes with respect to the skull should be determined accurately to be able to make a reliable diagnosis, and can require special skills. Together, these factors can complicate and slow down the starting of the EEG recording and, therefore, are rarely carried out in the field.

The body part of an exemplary embodiment of the disclosure is made of polyester film (Mylar). The electrical electrodes can be silver spirals (diameter 7 mm) connected to the end of conductive silver-plated insulated Aracon fibre. A good contact between the electrode and the skin is ensured by a hydrogel film (diameter 12-18 mm) developed for medical use. To facilitate skin attachment, a breathable tape part is attached around each electrode. By means of this matrix electrode, the following can be achieved: a significantly lighter and more flexible solution, which conforms better to the contours of the face and does not fold the skin; a stable electrode contact with the skin due to the highly adhesive hydrogel, and in this example, the skin tape support. In addition, this solution does not need strong compressive forces against the skin to function well. The electrical contact of the electrode is good and gel is not needed. In accordance with an exemplary embodiment, the contact between the silver wire and the gel can be optimized by means of the form and spiral structure of the wire, for example, improved breathability can be desirable, for example, with strongly perspiring patients. In accordance with an exemplary embodiment, the disclosed arrangement can include strongly attaching and extensive reference electrodes in the centerline, vertical and horizontal electrodes for eye movement for detecting artifacts, and the electrodes can be attached behind the ears to improve monitoring at the back of the skull.

The disclosure provides many alternative solutions regarding manufacturing techniques, choice of materials, number of electrodes and location of electrodes. The abovementioned can be quite optimal concerning the choice of materials and their functionality. In accordance with an exemplary embodiment, because the size and measurements of people's skulls can vary a great deal, an optimal solution takes also these into account and the sensor implementation can be easily made in a few basic sizes. For example, finding the correct position for the reference electrodes (for example, two electrodes) can successfully facilitate the analysis of the measuring data considerably by eliminating various artifacts, which can include, for example, confusing the electrical activity of muscles (EMG) due to eye movements with a measurable signal. In accordance with an exemplary embodiment, the type of electrode configuration according to the disclosure for the facial area (forehead, temples, bridge of nose) is not commercially available and thus the disclosure is new, and can include ease of use, inexpensiveness, disposability, simplicity and versatile reliable measurement.

In the following is further described a commercially viable solution representing a matrix electrode configuration according to the disclosure, where the matrix electrode configuration is a headset electrode configuration for implementing easy and rapid EEG monitoring. In accordance with an exemplary embodiment, with this headset electrode configuration, or headset, can be achieved solutions, which facilitate the phased mounting of the headset. The protective films of the electrode attachment surfaces of the headset can be divided into parts, and thus the headset can be attached in a controlled, phased manner on the face. The central forehead part can be attached into place first, after which the other parts can be attached on the right and left in phases, the furthest reaching parts last. By means of this headset electrode configuration can be also achieved integrated solutions for good contact and prevention of drying of the headset electrodes. Outside the actual electrical electrode configuration, and in the spaces within the electrode configuration, can be also parts adhering to the skin, which secure the attachment. Around the electrodes can be non-conductive attachment material, which can facilitate attachment and for its part can help prevent the electrode from drying. In accordance with an exemplary embodiment, the headsets can include a quick coupling solution, which allows a disposable sterile adapter to be connected to the headset. This coupling can be connected through a multipurpose adapter to different measuring devices. The headset can be thus suitable for use, as a sterile solution with couplings, with various kinds of devices. The package of the headset can be an important part of the product, which facilitates its use. In accordance with an exemplary embodiment, the package of the headset can contain, for example, clear illustrated numbered instructions, a picture of the typical placement of the headset on the face, the means needed for cleansing the face (wet wipes, cleansing tape, . . . ), the means for tying up the hair (if the hair would otherwise be in the way, for example net, headset, fastening clips, . . . ), a coupling, etc. For example, a measuring scale can be provided on the outer surface of the package. By means of the measuring scale on the package, sizing can be estimated (by trying the package on the patient's face), without opening the package, such that whether the model is suitable or whether a different modular size should be selected, which can help considerably in selecting the right size. On the EEG headset, for example, on the electrode configuration according to the disclosure, can be made a grounding layer isolated from the electrodes to diminish the induction of external electrical interferences to the wires and thus to the measured EEG signal.

Thus, it will be appreciated by those skilled in the art that the present invention can be embodied in other specific forms without departing from the spirit or essential characteristics thereof. The presently disclosed embodiments can be therefore considered in all respects to be illustrative and not restricted. The scope of the invention is indicated by the appended claims rather than the foregoing description and all changes that come within the meaning and range and equivalence thereof can be intended to be embraced therein.

What is claimed is:

1. An arrangement for carrying out electrode measurements on a surface of a skin of a patient's head for recording electrical activity of the brain, the arrangement, comprising:
   a matrix electrode configuration, which includes a body part of non-conductive material adapted to conform to contours of the surface of the skin, and which body part includes electrodes for producing measurement data;
   means for transmitting the measurement data connected to the body part;
   a measurement data unit for receiving the measurement data from the transmitting means for further processing of the measurement data,
   wherein the body part includes an electrode placement configuration for maintaining mutual placements of the electrodes with respect to one another, and the electrodes being configured to establish an electroconductive active attachment surface located between the electrodes and the surface of the skin for forming an electroconductive attachment contact between the electrodes and the surface of the skin for transmitting measurable signals from the patient's head to the electrodes through the electroconductive active attachment surface to produce measurement data, the electroconductive active attachment surface including hydrogel or other electroconductive adhesive material which adheres to the skin in order to form a stable and essentially interference-free attachment contact between the electrodes and the surface of the skin;

the matrix electrode configuration having at least two reference electrodes and at least two ground electrodes, wherein the matrix electrode configuration is configured for selection of any electrode combination including more than one each of the at least two reference electrodes and the at least two ground electrodes for producing the measurement data, and the electrodes of the matrix electrode configuration are of an optimized spiral structure configured to be in contact with hairless skin areas on the surface of the skin through the electroconductive active attachment layer, wherein the matrix electrode configuration is optimized through a relationship between the electroconductive active attachment surface and a non-conductive surface; and a grounding layer formed completely or partly over the body part to prevent external electrical interferences by isolating the grounding layer with an isolation layer from the electroconductive active attachment surface and the means for transmitting the measurement data.

2. The arrangement as claimed in claim 1, wherein the body part comprises:

an electrode placement configuration for maintaining the mutual placements of the electrodes with respect to one another for easy attachment of the matrix electrode configuration in the hairless skin areas of the patient's head by means of the active attachment surface, each electrode attaching to a measuring point in the hairless skin areas of the head.

3. The arrangement as claimed in claim 1, wherein the arrangement for carrying out electrode measurements comprises:

at least one electrode of the matrix electrode configuration being configured for attachment in the patient's chest area for carrying out cardiac measurements.

4. The arrangement as claimed in claim 1, wherein the matrix electrode configuration comprises:

two EOG electrodes, which identify eye movements.

5. The arrangement as claimed in claim 1, wherein the arrangement for carrying out electrode measurements comprises:

different sizes of matrix electrode configurations to fit different head sizes of patients.

6. The arrangement as claimed in claim 1, wherein the arrangement for carrying out electrode measurements is at least one of MRI and CT imaging compatible.

7. The arrangement as claimed in claim 1, comprising:

at least the matrix electrode configuration packed into a package, on an outside of which can be seen dimensioning indicators provided for ensuring a correct matrix electrode configuration size without opening the package.

8. A method for carrying out electrode measurements on a surface of a skin of a patient's head for recording electrical activity of the brain, the method, comprising:

placing a matrix electrode configuration on the surface of the skin of the patient head, wherein the matrix electrode configuration comprising:

a body part of non-conductive material conforming to contours of the surface of the skin, and which includes electrodes for producing measurement data connected to the body part, an electrode placement configuration for maintaining mutual placements of the electrodes with respect to one another, an electroconductive active attachment surface located between the electrodes and the surface of the skin for forming an electroconductive attachment contact between the electrodes and the surface of the skin for transmitting measurable signals from the patient's head to the electrodes through the electroconductive active attachment surface to produce measurement data, the electroconductive active attachment surface including hydrogel or other electroconductive adhesive material which adheres to the skin in order to form a stable and essentially interference-free attachment contact between the electrodes and the surface of the skin, the matrix electrode configuration having at least two reference electrodes and at least two ground electrodes, wherein the matrix electrode configuration is configured for selecting any electrode combination including more than one each of the at least two reference electrodes and the at least two ground electrodes for producing the measurement data, and the electrodes of the matrix electrode configuration are of an optimized spiral structure configured for being in contact with hairless skin areas of the surface of the skin through the electroconductive active attachment layer, the matrix electrode configuration is optimized through a relationship between the electroconductive active attachment surface and a non-conductive surface, and a grounding layer formed completely or partly over the body part to prevent external electrical interference by isolating the grounding layer with an isolation layer from the electroconductive active attachment surface and a means for transmitting the measurement data;

transmitting the measurement data connected to the electrodes of the body part to a measurement data unit; and receiving the measurement data on the measurement data unit and processing the measurement data.

9. The method as claimed in claim 8, wherein the body part comprises:

an electrode placement configuration for maintaining the mutual placements of the electrodes with respect to one another for easy attachment of the matrix electrode configuration in the hairless skin areas of the patient's head by means of the active attachment surface, each electrode attaching to a measuring point in the hairless skin areas of the head.

10. The method as claimed in claim 8, wherein the electroconductive active attachment surface includes an electroconductive surface and a non-conductive surface, the method comprising:

obtaining measurement data from the body part via the electroconductive active attachment surface.

11. The method as claimed in claim 8, wherein the matrix electrode configuration includes at least one electrode attached in the patient's chest area, the method comprising:

carrying out cardiac measurements via the at least one electrode.

12. The method as claimed in claim 8, wherein the matrix electrode configuration includes two EOG electrodes, the method comprising:
identifying eye movements via the EOG electrodes.

13. The method as claimed in claim 8, wherein an arrangement for carrying out electrode measurements includes different sizes of matrix electrode configurations, the method comprising:
fitting the matrix electrode configuration of a respective size to a head of a patient.

14. The method as claimed in claim 8, wherein an arrangement for carrying out electrode measurements includes at least two reference electrodes and at least two ground electrodes, the method comprising:
when measuring, selecting an electrode combination between the at least two reference electrodes and the at least two ground electrodes to produce the measurement data.

15. The method as claimed in claim 8, comprising:
carrying out electrode measurements via the matrix electrode configuration using at least one of MRI and CT imaging.

16. The method as claimed in claim 8, comprising:
packing at least the matrix electrode configuration into a package; and
providing dimensioning indicators on an outside of the package for ensuring a correct matrix electrode configuration size without opening the package.

* * * * *